US012797408B2

(12) United States Patent
Acharya et al.

(10) Patent No.: US 12,797,408 B2
(45) Date of Patent: Nov. 17, 2026

(54) OPHTHALMIC SOLUTION CONTAINING QUATERNARY CHITOSAN DERIVATIVES FOR TREATING OCULAR DISEASES

(71) Applicant: ClearSight Therapeutics, Dallas, TX (US)

(72) Inventors: Suchismita Acharya, Grapevine, TX (US); Nuria Jimenez, Colleyville, TX (US); Patrick Smale, Dallas, TX (US)

(73) Assignee: ClearSight Therapeutics, Dallas, TX (US)

( * ) Notice: Subject to any disclaimer, the term of this patent is extended or adjusted under 35 U.S.C. 154(b) by 0 days.

(21) Appl. No.: 19/380,414

(22) Filed: Nov. 5, 2025

(65) Prior Publication Data

US 2026/0124235 A1 May 7, 2026

Related U.S. Application Data

(60) Provisional application No. 63/717,628, filed on Nov. 7, 2024.

(51) Int. Cl.

| | |
|---|---|
| ***A61P 27/02*** | (2006.01) |
| ***A61K 9/00*** | (2006.01) |
| ***A61K 31/722*** | (2006.01) |
| ***A61K 47/02*** | (2006.01) |
| ***A61K 47/10*** | (2017.01) |
| ***A61K 47/34*** | (2017.01) |
| ***A61K 47/38*** | (2006.01) |

(52) U.S. Cl.

CPC .......... *A61K 31/722* (2013.01); *A61K 9/0048* (2013.01); *A61K 47/02* (2013.01); *A61K 47/10* (2013.01); *A61K 47/34* (2013.01); *A61K 47/38* (2013.01); *A61P 27/02* (2018.01)

(58) Field of Classification Search

CPC .... A61K 31/722; A61K 31/717; A61K 47/10; A61K 47/36; A61K 47/38; A61P 27/02; A61P 42/04; A61P 31/12

USPC .......................................................... 514/55

See application file for complete search history.

(56) References Cited

U.S. PATENT DOCUMENTS

| | | | |
|---|---|---|---|
| 4,365,050 | A | 12/1982 | Ivani |
| 4,396,625 | A | 8/1983 | Yamamori et al. |
| 4,826,826 | A | 5/1989 | Conti |
| 5,212,162 | A | 5/1993 | Missel et al. |
| 5,369,095 | A | 11/1994 | Kee et al. |
| 5,422,116 | A | 6/1995 | Yen et al. |
| 6,589,999 | B2 | 7/2003 | Gurny et al. |
| 7,220,422 | B2 | 5/2007 | First |
| 8,623,400 | B2 | 1/2014 | Liu et al. |
| 9,849,183 | B2 | 12/2017 | Liu et al. |
| 9,907,826 | B2 | 3/2018 | Simmons et al. |
| 10,279,005 | B2 | 5/2019 | Gore et al. |
| 2003/0031718 | A1 | 2/2003 | Wong et al. |
| 2005/0147584 | A1 | 7/2005 | Hughes et al. |
| 2006/0106104 | A1 | 5/2006 | Vehige et al. |
| 2010/0068300 | A1 | 3/2010 | Koverech et al. |
| 2012/0003323 | A1 | 1/2012 | Liu et al. |
| 2015/0044270 | A1 | 2/2015 | Mcdonnell et al. |
| 2015/0297731 | A1 | 10/2015 | Chiou et al. |
| 2017/0071895 | A1* | 3/2017 | Gamache ................ A61P 37/08 |
| 2020/0237925 | A1 | 7/2020 | Wei et al. |
| 2021/0177890 | A1* | 6/2021 | Pamel .................... A61K 33/20 |

FOREIGN PATENT DOCUMENTS

| | | | |
|---|---|---|---|
| WO | 2018177554 | A1 | 10/2018 |
| WO | 2018202783 | A1 | 11/2018 |
| WO | 2022087313 | A1 | 4/2022 |

OTHER PUBLICATIONS

Ghadermazi et al, Food Science & Nutrition, 2019, 7, 3363-3377.*
Rathapon Asasutjarit, et al.: Research Article: Development and Evaluation of Diclofenac Sodium Loaded-N-Trimethyl Chitosan Nanoparticles for Ophthalmic Use; AAPS PharmSciTech, vol. 16, No. 5, Oct. 2015; 12 pages.
Patent Cooperation Treaty: Invitation to Pay Additional Fees dated Jan. 5, 2026, in connection with International Application No. PCT/US2025/054188; Shane Thomas; 4 Pages.
Alcon Laboratories, Inc., Natacyn® (natamycin ophthalmic suspension) 5%, 2000, 2007 Alcon, Inc., Revised: May 2008, 3 pages.
Allyn, Megan M et al. "Considerations for Polymers Used in Ocular Drug Delivery." Frontiers in medicine vol. 8 787644. Jan. 28, 2022, doi:10.3389/fmed.2021.787644.
Arun Teotia, et al., " Quaternized Chitosan Derivatives as Viable Antiviral Agents: Structure-Activity Correlations and Mechanisms of Action" ACS Applied Materials & Interfaces 2023 15 (15), 18707-18719, DOI: 10.1021/acsami.3c01421.
Azari, Amir A, and Neal P Barney. "Conjunctivitis: a systematic review of diagnosis and treatment." JAMA vol. 310, 16 (2013): 1721-1729. doi:10.1001/jama.2013.280318.
Binder, Alison M et al. "Human Adenovirus Surveillance—United States, 2003-2016." MMWR. Morbidity and mortality weekly report vol. 66,39 1039-1042. Oct. 6, 2017.
Chiang, Y P et al. "Office visits to ophthalmologists and other physicians for eye care among the U.S. population, 1990." Public health reports (Washington, D.C. : 1974) vol. 110,2 (1995): 147-53.
De Britto, Douglas et al. "Quaternary Salts of Chitosan: History, Antimicrobial Features, and Prospects." International Journal of Carbohydrate Chemistry 2011 (2011): 1-12. International Journal of Carbohydrate Chemistry.

(Continued)

*Primary Examiner* — Ganapathy Krishnan
(74) *Attorney, Agent, or Firm* — Gregory M. Howison

(57) ABSTRACT

A pharmaceutical composition to be applied to an ocular surface is disclosed that includes a quaternized chitosan derivative to provide antimicrobial activity against gram-negative bacteria, gram-positive bacteria, fungi, and viruses as an active ingredient. This is combined with a cellulose compound acting as a viscosity agent and demulcent to protect and lubricate mucous membrane surfaces. This is further combined with a humectant and tonicity agent to retain moisture on the ocular surface and maintain a comfortable osmolarity for the eye. This is further combined with a buffer/pH adjuster system configured to support a physiologically tolerable pH of about 6.0 to 8.0. Finally, this is combined with purified water as a diluent.

26 Claims, 5 Drawing Sheets

(56) References Cited

OTHER PUBLICATIONS

Fattah, Rana Abdel Fattah Abdel et al. "Effect of chitosan nanoparticles on quorum sensing-controlled virulence factors and expression of Lasl and RhlI genes among Pseudomonas aeruginosa clinical isolates." AIMS microbiology vol. 7,4 415-430. Oct. 26, 2021, doi: 10.3934/microbiol.2021025.
Freitas ED, Moura Jr. CF, Kerwald J, Beppu MM. An Overview of Current Knowledge on the Properties, Synthesis and Applications of Quaternary Chitosan Derivatives. Polymers. 2020; 12(12):2878. https://doi.org/10.3390/polym12122878.
Garratt, Susan, Conjunctivitis Preferred Practice Pattern®, American Academy of Ophthalmology, Sep. 22, 2023, pp. P135-P204.
Hong Tang, et al., "Antibacterial action of a novel functionalized chitosan-arginine against Gram-negative bacteria" Acta Biomater, vol. 6, Issue 7, 2010, pp. 2562-2571, https://doi.org/10.1016/j.actbio.2010.01.002.
Labib, Bisant A et al. "Management of Adenoviral Keratoconjunctivitis: Challenges and Solutions." Clinical ophthalmology (Auckland, N.Z.) vol. 14 837-852. Mar. 17, 2020.
Luan F, Wei L, Zhang J, Tan W, Chen Y, Dong F, Li Q, Guo Z. Preparation and Characterization of Quaternized Chitosan Derivatives and Assessment of Their Antioxidant Activity. Molecules. 2018; 23(3):516. https://doi.org/10.3390/molecules23030516.
Matica, Mariana Adina et al. "Chitosan as a Wound Dressing Starting Material: Antimicrobial Properties and Mode of Action." International journal of molecular sciences vol. 20,23 5889. Nov. 24, 2019, doi: 10.3390/ijms20235889.
Messina, Marco, and Harminder S Dua. "Early results on the use of chitosan-N-acetylcysteine (Lacrimera®) in the management of dry eye disease of varied etiology." International ophthalmology vol. 39,3 (2019): 693-696. doi:10.1007/s10792-018-0843-0.
Nepp, Johannes et al. "Management of moderate-to-severe dry eye disease using chitosan-N-acetylcysteine (Lacrimera®) eye drops: a retrospective case series." International ophthalmology vol. 40,6 (2020): 1547-1552. doi:10.1007/s10792-020-01324-5.
Rossi, Tommaso et al. "Cataract surgery practice patterns worldwide: a survey." BMJ open ophthalmology vol. 6,1 e000464. Jan. 13, 2021, pp. 1-9, doi: 10.1136/bmjophth-2020-000464.
Sarhan, Afaf. (2019). Characterization of Chitosan and Polyethylene glycol Blend Film. Egyptian Journal of Chemistry. vol. 62, pp. 405-412.
Smith, A.F., Waycaster, C. Estimate of the direct and indirect annual cost of bacterial conjunctivitis in the United States. BMC Ophthalmol 9:13, Nov. 25, 2009, https://doi.org/10.1186/1471-2415-9-13.
Sueke, Henri et al. "Minimum inhibitory concentrations of standard and novel antimicrobials for isolates from bacterial keratitis." Investigative ophthalmology & visual science vol. 51,5 (2010): 2519-24.
Szymańska, Emilia, and Katarzyna Winnicka. "Stability of chitosan-a challenge for pharmaceutical and biomedical applications." Marine drugs vol. 13,4 1819-46. Apr. 1, 2015, doi: 10.3390/md13041819.
Teweldemedhin, Mebrahtu et al. "Bacterial profile of ocular infections: a systematic review." BMC ophthalmology vol. 17,1 212. Nov. 25, 2017.
Thomas, Philip A. "Current perspectives on ophthalmic mycoses." Clinical microbiology reviews vol. 16,4 (2003): 730-97.
U.S. Food and Drug Administration, "Final Administrative Order (OTC000023)—Over-the-Counter Monograph M018: Ophthalmic Drug Products for Over-the-Counter Human Use", Apr. 4, 2022, pp. 1-13.
Zamboulis A, Nanaki S, Michailidou G, Koumentakou I, Lazaridou M, Ainali NM, Xanthopoulou E, Bikiaris DN. Chitosan and its Derivatives for Ocular Delivery Formulations: Recent Advances and Developments. Polymers. 2020; 12(7):1519. https://doi.org/10.3390/polym12071519.
Zegans, Michael E et al. "Clinical features, outcomes, and costs of a conjunctivitis outbreak caused by the ST448 strain of *Streptococcus pneumoniae*." Cornea vol. 28,5 (2009): 503-9. doi: 10.1097/ICO.0b013e3181909362.
Zhang, Jingjing et al. "Synthesis of Quaternary Ammonium Salts of Chitosan Bearing Halogenated Acetate for Antifungal and Antibacterial Activities." Polymers vol. 10,5 530. May 15, 2018, doi: 10.3390/polym10050530.
Ziyun Fang, Wenjie Cong, Hualan Zhou, Jianguo Zhang, Mingxuan Wang, Biological activities, mechanisms and applications of chitooligosaccharides in the food industry,Journal of Functional Foods, vol. 116, 2024,106219,ISSN 1756-4646, https://doi.org/10.1016/j.jff.2024.106219.
Taskapili, M. et al.) Pediatric conjunctivitis. Turkish Archives of Pediatrics, vol. 4 7, 2012, DOI: 10.4274/tpa.927, pp. 237-243.
Patent Cooperation Treaty: International Search Report and Written Opinion for PCT/US25/54188 (related application); Shane Thomas; Mar. 2, 2026; 23 pages.

* cited by examiner

TRIMETHYL CHITOSAN (TMC)

N-(2-HYDROXY) PROPYL-3-TRIMETHYLAMMONIUM CHITOSAN (HTCC)

OPHTHALMIC SOLUTION CONTAINING QUATERNARY CHITOSAN DERIVATIVES FOR TREATING OCULAR DISEASES

CROSS-REFERENCE TO RELATED APPLICATIONS

This application claims the benefit of U.S. Provisional Application No. 63/717,628, filed Nov. 7, 2024, entitled STERILE AQUEOUS OPHTHALMIC SOLUTION CONTAINING QUATERNARY CHITOSAN DERIVATIVES FOR TREATING ACUTE INFECTIOUS CONJUNCTIVITIS, the specifications of which are incorporated by reference herein in their entirety.

TECHNICAL FIELD

This disclosure relates to a sterile ophthalmic solution containing a quaternary chitosan derivative.

BACKGROUND

Conjunctivitis, or inflammation of the conjunctiva, is a general term that refers to a diverse group of diseases/disorders that affect primarily the conjunctiva. Most varieties of conjunctivitis are self-limited, but some progress and may cause serious ocular and extraocular complications. Conjunctivitis can be classified as noninfectious or infectious and as acute, chronic, or recurrent. Noninfectious types of conjunctivitis include allergic, mechanical/irritative/toxic, immune-mediated, and neoplastic, and these types may overlap. The causes of infectious conjunctivitis include viruses, fungi, and bacteria.

Acute Conjunctivitis ("Pink Eye") is the inflammation of the lining of the eyelids and eyeball caused by bacteria, viruses, allergic or immunological reactions, mechanical irritation, or medicines.

Conjunctivitis is a diagnosis that encompasses a diverse group of diseases that occur worldwide and affect all ages, all social strata, and all genders. Although there are no reliable figures that document the incidence or prevalence of all forms of conjunctivitis, this condition has been recognized as one of the most frequent causes of patient self-referral. It represents four million annual cases in the US treated with antibiotic eyedrops as the standard of care, with $1.9 billion in estimated lost wages annually in the US due to 8.5 million missed workdays and 3.5 million missed school days. The current treatment practice for acute conjunctivitis includes topical mast cell stabilizers, antihistamines, and topical antibiotics. It is highly contagious and prevalent in children. Eighty percent or more of the acute infectious conjunctivitis cases have a viral cause, for which the current practice of using antibiotics is inefficient and requires a prescription from a physician. In addition, the overuse of antibiotics creates resistance, making the treatment even less effective.

This acute infectious conjunctivitis, especially epidemic keratoconjunctivitis (EKC), additionally poses a serious and ongoing threat to force health protection and mission readiness in the U.S. military. As the condition is highly contagious, often caused by adenoviruses, it can spread quickly in communal and operational settings such as barracks, naval vessels, and field deployments. EKC alone accounts for 13.3% of all conjunctival issues and 47.7% of ocular medical encounters among active-duty personnel, significantly impairing unit readiness and increasing the need for isolation. The clinical course involves a seven-day incubation period, followed by weeks of contagiousness. During deployments or shipboard confinement, where isolation is impractical, outbreaks can compromise entire units. EKC is predominantly viral (~80%), with adenovirus identified in 65-90% of cases. Despite the operational impact, there are no FDA-approved antiviral treatments for adenoviral conjunctivitis, and current care remains mostly palliative, failing to shorten the duration of the disease or its transmissibility. This creates a critical capability gap in the management of ocular infections during military operations.

Currently, treatment for EKC and other acute infectious conjunctivitis relies on supportive care, including cold compresses, antibiotics, lubricating drops, and hygiene education. In severe or complicated cases, off-label therapies such as povidone-iodine rinses, corticosteroids, and antiviral gels (e.g., ganciclovir) may be used. However, there is limited evidence of their effectiveness against adenovirus, and potential risks of side effects exist. The complex causes of EKC, involving viral, bacterial (such as Methicillin-resistant *Staphylococcus aureus* or MRSA), inflammatory factors, and corneal damage, require a comprehensive treatment approach. Current therapies do not target all the main aspects of EKC: viral replication, bacterial superinfection, inflammation, and ongoing mucosal colonization. Moreover, the increasing prevalence of antibiotic resistance and the absence of any FDA-approved ophthalmic drugs in the U.S. exacerbate therapeutic challenges.

Conjunctivitis rarely causes permanent visual loss or structural damage, but its economic impact is considerable, largely due to lost work or school time and the costs of medical visits, testing, and treatment.

SUMMARY

The present invention, disclosed in one aspect herein, comprises a pharmaceutical composition to be applied to an ocular surface that includes a quaternary chitosan derivative as an active ingredient, providing antimicrobial activity against gram-negative bacteria, gram-positive bacteria, fungi, and viruses. This is combined with a cellulosic compound acting as a viscosity agent and demulcent to protect and lubricate mucous membrane surfaces. This is further combined with a humectant and tonicity agent to retain moisture on the ocular surface and maintain a comfortable osmolarity for the eye. This is further combined with a buffer/pH adjuster system configured to maintain a physiologically tolerable pH of about 6.0 to 8.0. Finally, this is combined with purified water as a diluent.

BRIEF DESCRIPTION OF THE DRAWINGS

For a more complete understanding, reference is now made to the following description taken in conjunction with the accompanying Drawings, in which.

DETAILED DESCRIPTION

Figure 1:
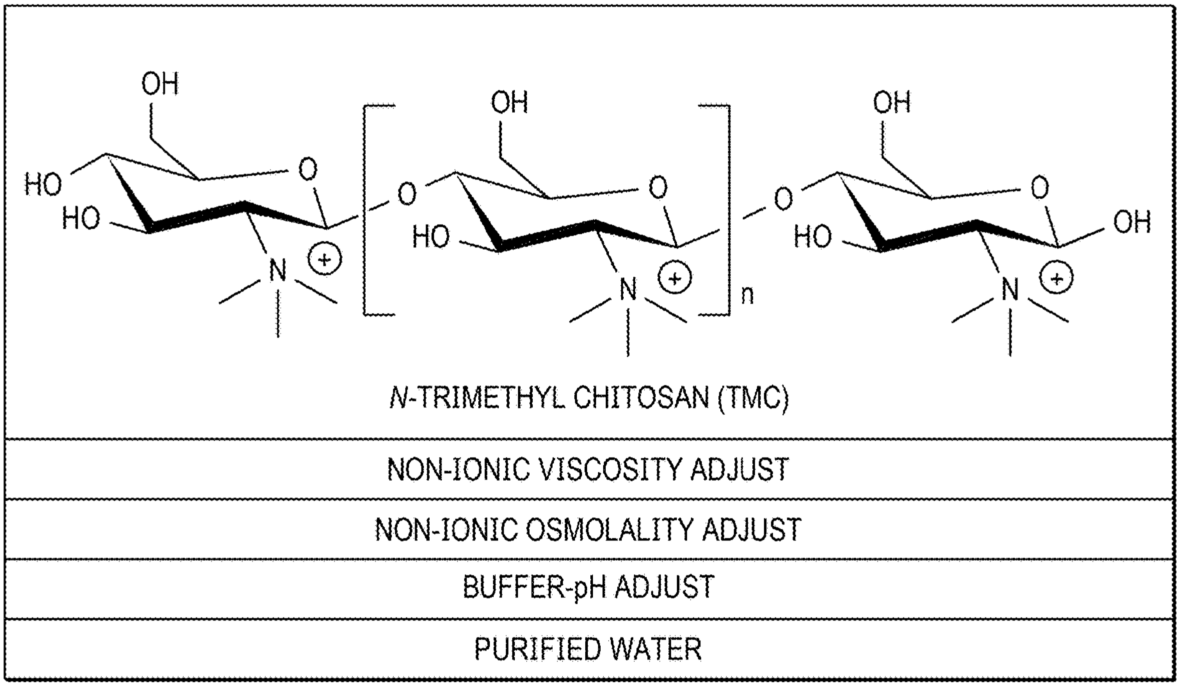
FIG. 1 illustrates a diagrammatic view of the eyedrop composition of the present disclosure.
Figure 2:
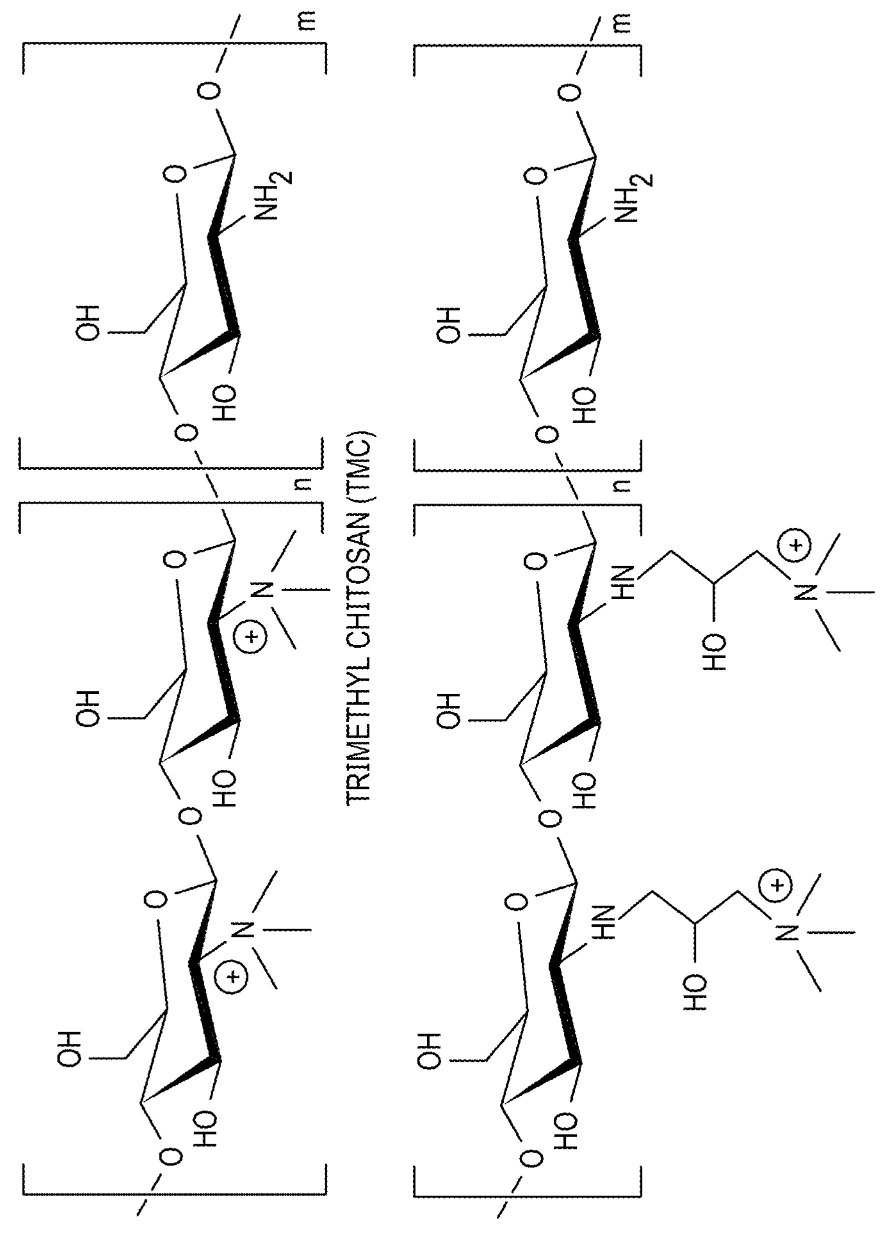
FIG. 2 illustrates a graphical presentation of the chemical structure of quaternized chitosan (CS) derivatives (TMC, HTCC)

Referring now to the drawings, wherein like reference numbers are used herein to designate like elements throughout, the various views and embodiments for a Sterile Aqueous Ophthalmic Solution Containing Quaternary Chitosan Derivatives for treating acute infectious conjunctivitis are illustrated and described, and other possible embodiments are described. The figures are not necessarily drawn to scale, and in some instances the drawings have been exaggerated and/or simplified in places for illustrative purposes only. One of ordinary skill in the art will appreciate the many possible applications and variations based on the following examples of possible embodiments.

The disclosure relates to a sterile ophthalmic solution containing a quaternary chitosan derivative with broad-spectrum antimicrobial properties for the treatment of acute conjunctivitis ("Pink Eye") in the eye. The disclosure also relates to the use of a quaternary chitosan derivative of FORMULA-I in Appendix below to treat acute infectious conjunctivitis in the eye (f.i. N-(2-Hydroxy) propyl-3-trimethylammonium chitosan chloride, trimethyl chitosan).

Chitosan (CS) is a semi-synthetic cationic linear polysaccharide made of randomly distributed D-glucosamine and N-acetyl-D-glucosamine units, linked via β-(1→4) glycoside bonds. It is synthesized by the deacetylation of chitin. CS is water-soluble in acidic pH due to the protonation of the free amino groups, non-toxic, highly biocompatible, and biodegradable, with low immunogenicity. Additionally, CS has inherent antibacterial properties and a mucoadhesive character and can disrupt epithelial tight junctions, thus acting as a permeability enhancer. CS and its derivatives are well-suited for the challenging field of ocular drug delivery.

Chitosan was classified as GRAS (Generally Recognized As Safe) by the FDA and approved by ECHA (European Chemical Agency). It has been approved by the FDA only as a food additive and a wound dressing.

CS has antimicrobial activity, or by permeating into the microbial plasma membrane. The mechanism is based on interactions taking place between the positively charged amino groups of CS and the negatively charged microbial cell membranes. These ionic interactions disrupt the microbial membrane, ultimately resulting in a leakage of intracellular constituents. The concentration of CS is important, as at concentrations <0.2 mg/mL, its amino groups interact with the negatively charged bacterial surface, leading to agglutination. At higher concentrations, the number of CS amino groups is too high and can form a net positive charge on the bacterial surfaces, resulting in a suspension.

Quaternization of chitosan, i.e., a CS derivative, can result in derivatives with enhanced antibacterial properties against several gram-negative and gram-positive bacteria compared to neat chitosan. These derivative compounds have quaternary amines, which are positively charged in their structure, increasing electrostatic interactions with the negatively charged outer layers of microbial cell walls. Through this physical association, the polymer forms a strong, adherent complex on the microbial surface, destabilizing the cell envelope and thereby compromising its structural integrity. This physical disruption results in the release of cellular content and loss of viability of the microbes. The higher the degree of quaternization or the higher the content of quaternary amines in the polymer, the higher the antimicrobial activity is expected. Another advantage of quaternized chitosan is its improved aqueous solubility compared to chitosan, facilitating the formulation of eye drops.

As disclosed herein, quaternary chitosan derivatives such as N-(2-Hydroxy)propyl-3-trimethylammonium chitosan chloride (HTCC) and trimethyl chitosan (TMC) are incorporated into an eyedrop dosage form. These, apart from their use in eyedrops, are previously not known to treat acute and epidemic infectious and non-infectious conjunctivitis. These formulations are designed to have broad-spectrum antimicrobial efficacy against both gram-negative and gram-positive bacteria, viruses, and fungi, addressing most cases in children and immunocompromised older adults.

The quaternary chitosan disclosed in one embodiment herein is formulated as sterile eyedrops, in a viscous solution containing hydroxypropyl methylcellulose or any other cellulosic component described in the Ophthalmic OTC monograph as active demulcent. The remaining excipients are recognized as safe for topical application to the eye.

Referring to FIG. 1, a diagrammatic view of one embodiment of the eyedrop is illustrated. The base of the eyedrop solution is comprised of purified water. Added to the purified water is a non-ionic cellulose compound acting as a viscosity agent and demulcent to protect and lubricate mucous membrane surfaces, a non-ionic humectant and tonicity agent to retain moisture on the ocular surface and maintain a comfortable osmolarity for the eye and a buffer/pH adjuster system configured to maintain a physiologically tolerable pH of about 6.0 to 8.0. To this compound is added, in this disclosed embodiment, a CS derivative of TMC (note that HTCC, as a CS derivative, could also be substituted) present in an amount effective to provide antimicrobial activity against gram-negative bacteria, gram-positive bacteria, fungi, and viruses. As will be disclosed herein, the components of the eye drop are varied to maintain a correct viscosity, osmolarity, and pH to provide an eyedrop that will not irritate the ocular surface and not result in any degradation of the CS derivative. TMC and HTCC can degrade due to several factors, the main one being hydrolysis, to yield a stable eyedrop that maintains sufficient antimicrobial activity against gram-negative bacteria, gram-positive bacteria, fungi, and viruses over time.

In general, the ophthalmic solution is comprised of an eye drop with the addition of the chitosan derivative, TMC or HTCC. These chitosan derivatives do not affect the properties of the eyedrops nor do the excipients that comprise the eyedrop affect or improve the efficacy of the chitosan derivative. Rather, the eyedrop is the delivery mechanism for the chitosan derivative to the mucal surface such as the ocular surface. The excipients that comprise the eyedrop are selected to essentially protect the integrity of the chitosan derivative. By minimizing the degradation of the chitosan derivative due to such factors as hydrolysis or cleavage, the number of active amine sites are preserved to extend the shelflife of the product and also to extend the presence of the active amine sites on the ocular surface after application.

Hydrolysis is one pathway for the degradation of CS derivatives. Hydrolysis refers to the chemical breakdown of a compound by reaction with water, leading to the cleavage of chemical bonds. For TMC, hydrolysis can occur under acidic or basic conditions, releasing trimethylamine and regenerating chitosan and small chitosan fragments. Factors influencing the hydrolysis of TMC include pH level (acidic or basic conditions accelerate hydrolysis), high temperatures (which can increase the rate of hydrolysis), the concentration of TMC in solution, and time. Additionally, the purity of the TMC is a factor, as it is derived from sources such as seashells and the like, and some metals may be present that can accelerate hydrolysis. Ionic materials can also accelerate hydrolysis. As will be disclosed and discussed below, the goal is to reduce TMC degradation by using non-ionic excipients and maintaining the formulation pH as close to neutral as possible.

As disclosed herein in one embodiment, the quaternary chitosan derivatives utilized are N-(2-Hydroxy) propyl-3-trimethylammonium chitosan chloride (HTCC) or trimethyl chitosan (TMC) in an eyedrop dosage form that has not been previously utilized for the use of treating acute and epidemic infectious conjunctivitis in the eye, and that will have broad-spectrum antimicrobial efficacy against both gram-negative and gram-positive bacteria, viruses and fungi, addressing most of the cases in children and immunocompromised older adults.

Additionally, the disclosed quaternary chitosan compounds provide a secondary physical mechanism of action (MOA) by interfering with microbial surface communication. By forming a physical coating around microbial clusters, the material limits their ability to assemble into coordinated communities, thereby reducing motility, biofilm formation, and surface adherence. This effect decreases the likelihood of colonization and the progression of infection, achieved through surface-level physical inhibition rather than chemical modification.

The positively charged quaternary amines within the chemical structure of the disclosed polymers enable the compound to dissolve in water across a wide pH range (2-12). They are more stable at slightly acidic to neutral pH (6.0-7.5), making them more suitable for ocular delivery as a liquid eye drop solution with a pH tolerable for the eye. Regular chitosan only dissolves in acidic conditions (below pH 5.5, using 2% acetic acid) because the amino groups become protonated, but such pH levels are not tolerable for the eye.

The quaternary chitosan derivatives in the disclosed eyedrop are formulated as sterile eyedrops, with a viscous solution containing hydroxypropyl methylcellulose or any other cellulosic component described in the Ophthalmic OTC monograph as an active demulcent. The rest of the excipients are recognized to be safe to apply topically in the eye and selected to stabilize the quaternary chitosan derivative in aqueous solution.

The disclosed solution achieves a desired stability from: (i) viscosity-mediated kinetic stabilization and mild steric or anti-adsorptive effects provided by nonionic cellulosics; (ii) PEG-400 (polyethylene glycol 400) humectancy that maintains hydration and decreases interchain hydrogen bonding of the cationic chitosan derivative; and (iii) a low-ionic-strength, borate-based buffer that prevents harmful polyelectrolyte complexation. These combined features enable improved optical clarity and stable pH, osmolality, and viscosity during storage, while maintaining the compound's chemical structure and antimicrobial activity.

Referring back to the eyedrop solution depicted in FIG. 1, the CS derivative disclosed is based on Chitosan, which, along with the quaternary chitosan derivatives, is known for its antimicrobial properties for wound healing and biomedical applications. Such applications involve irrigating wounds with a freshly prepared saline solution of Chitosan or its derivatives to avoid degradation and possible loss of activity. The disclosed embodiment is directed to the use of the Chitosan derivatives as an ocular surface-friendly eye drop with improved stability to treat acute and epidemic infectious conjunctivitis in the eye.

The disclosed eyedrop is directed, in one disclosed application, for treating acute infectious conjunctivitis ("Pink Eye"), thereby offering significant value for parents and patients due to its effective treatment, safety, and efficiency. The efficacy is improved because it targets all forms of infectious conjunctivitis (fungal, viral, and bacterial). The product is safe because there is no risk of overuse due to antibiotic resistance.

The composition disclosed herein provides a broad-spectrum therapeutic option for ophthalmic irritation caused by bacterial, fungal, or viral conjunctivitis. The current standard of care (SOC) for bacterial conjunctivitis is antibiotic eye drops, which pose risks of antimicrobial resistance and toxicity. This disclosed composition circumvents those risks by treating bacterial conjunctivitis through a different mechanism of action that does not affect the microorganism's genetic material but instead disrupts the cell membrane, causing leakage of intracellular contents.

It also provides an eye drop for alleviating symptoms associated with fungal and viral conjunctivitis, both of which currently lack SOC treatment options.

The disclosed formulation is a sterile ophthalmic solution containing a quaternary chitosan derivative, such as N-(2-hydroxypropyl)-3-trimethylammonium chitosan chloride or trimethyl chitosan, used as a broad-spectrum antimicrobial effective against both gram-negative and gram-positive bacteria, viruses, and fungi. The excipients selected to improve mucoadhesion to the ocular surface and to enhance the formulation's stability are carefully chosen. The excipients used have previously demonstrated safety in ophthalmic eye drops and are included in the FDA Ophthalmic Monograph M018 for over-the-counter use. The disclosed eye drop contains a non-ionic cellulosic compound, such as one of hydroxypropyl methylcellulose or hydroxyethyl cellulose, as a viscosity agent and demulcent, used to protect and lubricate mucous membrane surfaces and relieve dryness and irritation. Also, it includes a non-ionic humectant and tonicity agent, such as polyethylene glycol, to retain moisture on the ocular surface and maintain a comfortable osmolarity. It contains another non-ionic tonicity agent such as mannitol provided to adjust the osmolality of the humectant and tonicity agent, a low ionic buffer such as boric acid, and a pH adjuster, such as sodium chloride and hydrochloric acid, to target a tolerated pH range for the eye (6.0-8.0). The general diluent is purified water.

A list of ingredients is listed in Table 1 as Follows:

TABLE 1

| Ingredients | Function |
|---|---|
| Trimethyl chitosan (TMC) | Antimicrobial |
| N-(2-Hydroxy) propyl-3-trimethylammonium chitosan chloride (HTCC) | Antimicrobial |

TABLE 1-continued

| Ingredients | Function |
|---|---|
| Hydroxypropyl Methylcellulose (HPMC) | Viscosity agent and demulcent |
| Hydroxyethyl cellulose (HEC) | Viscosity agent and demulcent |
| Polyethylene Glycol 400 | Humectant and tonicity agent |
| Mannitol | Tonicity agent |
| Boric Acid | Buffer |
| Sodium Hydroxide or Hydrochloric Acid | pH adjuster |
| Purified water | Diluent |

With reference to Table 1, the antimicrobial is TMC or HTCC. To maintain viscosity at no more than 250 mPa·s, an acceptable range for an ocular solution delivered to the eye as an eyedrop, One of Hydroxypropyl Methylcellulose (HPMC) or Hydroxyethyl cellulose (HEC) are utilized as non-ionic humectant and tonicity agents. HPMC and/or HEC can provide adequate wetting for use as an eye drop with contact lenses, and are used to adjust the viscosity of the overall solution to compensate for the addition of the CS derivative. Polyethylene Glycol 400 is the primary non-ionic tonicity agent, with Mannitol utilized to adjust the tonicity to achieve the desired osmolality of 220 to 320 mOsm/Kg. The Boric acid as a low ionic buffer and Sodium Hydroxide/Hydrochloric acid as a pH adjuster, enabling adjustment of the eye drop solution to be adjusted to as close to neutral at 7.0 as possible, with a range of 6.0-7.5.

As pharmaceutical products with chitosan and chitosan derivatives are highly susceptible to chemical and physico-chemical degradation upon storage, the objective is to add excipients to improve the quaternized chitosan-based system's stability.

Nonionic cellulosic polymers, such as Hydroxypropyl Methylcellulose (HPMC) and Hydroxyethyl cellulose (HEC), stabilize quaternized chitosan derivatives through viscosity-mediated kinetic stabilization and a gentle steric effect, without ionic incompatibility.

The addition of polyols (mannitol, sorbitol, and glycerol) to chitosan derivatives protects their molecular weight, viscosity, and thermogelling properties. This phenomenon is attributed to the formation of a protective hydration layer around chitin chains via interchain hydrogen bonds.

The polyethylene glycol 400 is used as a humectant and tonicity agent. It forms hydrogen bonds with the quaternary chitosan derivative, slightly disrupting intra-polymer hydrogen bonds and mitigating aggregation of chitosan derivative over shelf life, thus improving stability of the final product in solution. This is important because chitosan derivatives involve long polymer chains of quaternized amines which are prone to aggregation, resulting in precipitation in the solution.

Boric acid is a weak buffer, contributes only low ionic strength, and complexes with polyols (mannitol, sorbitol, glycerol) at neutral or close to neutral pH for comfort to the eye, and to avoid acid- or base-catalyzed polysaccharide degradation. Quaternized chitosans (TMC or HTCC) remain cationic and water-soluble across neutral pH, and thus maintaining this pH preserves their solution behavior and antimicrobial performance.

The following non-limiting examples illustrate certain aspects of the present disclosed embodiment.

Example 1

A fractional multi-factorial design of experiments with 4 factors and 2 levels, involving a total of 8 formulations (Table 2—compositions), was conducted to study the effects of pH, viscosity agent, quaternary chitosan derivative, and ionic strength on the physicochemical characteristics of the formulation (appearance [color and clarity], viscosity, pH, and osmolality). The study design and responses (physico-chemical parameters) are shown in Table 3.

TABLE 2

| | Concentration (% w/w) | | | | | | | |
|---|---|---|---|---|---|---|---|---|
| Ingredients | A | B | C | D | E | F | G | H |
| TMC [a] | 0.1 | 0.1 | 0.1 | 0.1 | — | — | — | — |
| HTCC [b] | — | — | — | — | 0.1 | 0.1 | 0.1 | 0.1 |
| HPMC E4M Premium 2910 [c] | 1 | 1 | | | 1 | 1 | | |
| HEC 250HX [d] | — | — | 1 | 1 | | | 1 | 1 |
| Polyethylene Glycol 400 | 1 | 1 | 1 | 1 | 1 | 1 | 1 | 1 |
| Mannitol | 2.8 | 2.4 | 2.4 | 2.8 | 2.4 | 2.8 | 2.8 | 2.4 |
| Boric Acid | 0.15 | 0.3 | 0.3 | 0.15 | 0.3 | 0.15 | 0.15 | 0.3 |
| Sodium hydroxide or hydrochloric acid 1N | q.s to 6.3 | q.s to 7.0 | q.s to 6.3 | q.s to 7.0 | q.s to 6.3 | q.s to 7.0 | q.s to 6.3 | q.s to 7.0 |
| Purified water | q.s to 100 | q.s to 100 | q.s to 100 | q.s to 100 | q.s to 100 | q.s to 100 | q.s to 100 | q.s to 100 |

[a] Trimethyl chitosan;

[b] N-(2-Hydroxy) propyl-3-trimethylammonium chitosan chloride;

[c] Hydroxypropyl Methylcellulose (HPMC);

[d] Hydroxyethyl cellulose.

TABLE 3

| | Factors | | | | | | | | |
|---|---|---|---|---|---|---|---|---|---|
| | | | Ionic | Matrix symbols | | | Response | | |
| Run Order | Chitosan Derivative | Viscosity agent | strength (%) | Chitosan Derivative | Viscosity agent | Ionic Strength | pH | Osmolality (mOsm/Kg) | Viscosity (mPa · s) |
| 1 | TMC [(a)] | HPMC [(c)] | 0.15 | 1 | 1 | −1 | 7.25 | 309 | 259 |
| 2 | TMC | HPMC | 0.3 | 1 | 1 | 1 | 6.76 | 338 | 269 |
| 3 | TMC | HEC [(d)] | 0.3 | 1 | −1 | 1 | 6.47 | 364 | 230 |
| 4 | TMC | HEC | 0.15 | 1 | −1 | −1 | 7.13 | 256 | 257 |
| 5 | HTCC [(b)] | HPMC | 0.3 | −1 | 1 | 1 | 6.55 | 226 | 246 |
| 6 | HTCC | HPMC | 0.15 | −1 | 1 | −1 | 7.18 | 202 | 168 |
| 7 | HTCC | HEC | 0.15 | −1 | −1 | −1 | 6.47 | 232 | 293 |
| 8 | HTCC | HEC | 0.3 | −1 | −1 | 1 | 7.14 | 166 | 235 |

[(a)] Trimethyl chitosan;
[(b)] N-(2-Hydroxy) propyl-3-trimethylammonium chitosan chloride;
[(c)] Hydroxypropyl Methylcellulose;
[(d)] Hydroxyethyl cellulose The factorial design analysis aimed to investigate the relationship between the factors and their interactions with the responses using factorial regression. CS derivative is the main effect and the only one statistically significant with a positive impact on pH (coefficient 0.2138; p-value<0.05). The model explains 99.74% of the variation for pH, indicating an excellent fit. The adjusted R-sq value of 98.19% confirms the model's robustness. Based on the results, all prepared formulations were clear, colorless, and physicochemically stable.

The compounding procedure for formulations A-H in Table 2 is as follows:

1. In a previously tarred glass compounding vessel, weigh purified water corresponding to 50% of the total batch size.
2. Weigh TMC or HTCC in a paper and slowly add it to the compounding vessel in step 1 under continuous magnetic agitation to avoid agglomeration of excipient particles. Agitate until complete dissolution, and annotate the time required.
3. Weigh and add 37.5 g of HPMC or HEC stock solution (2%) to the compounding vessel in step 2 under continuous magnetic agitation until complete homogenization.
4. Weigh and add Polyethylene Glycol (PEG) 400 to the compounding vessel in step 3 under continuous agitation until complete dissolution.
5. Weigh and add Mannitol to the compounding vessel in step 4 under continuous agitation until complete dissolution.
6. Weigh and add Boric acid to the compounding vessel in step 5 under continuous agitation until complete dissolution.
7. Check the pH and adjust to the target pH±0.1 with the required amount of NaOH 1N/HCl 1N.
8. Add purified water to QS to the final weight and mix until homogeneous.

Example 2

TMC showed greater water solubility than HTCC and was selected to prepare the following four formulations (Table 4) for a 3-month stability study.

TABLE 4

| | Concentration (% w/w) | | | |
|---|---|---|---|---|
| Ingredients | J | K | L | M |
| TMC [(a)] | 0.1 | 0.1 | 0.1 | — |
| HTCC [(b)] | — | — | — | 0.1 |
| HEC 250HX [(d)] | — | 0.75 | 0.75 | 0.75 |
| HPMC E4M Premium 2910 [(c)] | 0.75 | — | — | — |
| PEG400 | 1 | 1 | 1 | 1 |
| Mannitol | 2.8 | 2.8 | 2.8 | 2.8 |
| Boric Acid | 0.15 | 0.15 | 0.15 | 0.15 |
| NaOH or HCL | q.s to pH 7.0 | q.s to pH 7.0 | q.s to pH 6.3 | q.s to pH 6.3 |
| Purified water | q.s to 100 | q.s to 100 | q.s to 100 | q.s to 100 |

[(a)] Trimethyl chitosan;
[(b)] N-(2-Hydroxy) propyl-3-trimethylammonium chitosan chloride;
[(c)] Hydroxypropyl Methylcellulose;
[(d)] Hydroxyethyl cellulose The compositions J-M were prepared sterile in a two-step compounding procedure as follows:

1. TMC is dissolved in 45% purified water and then filtered by a 0.22μ polyvinylidene fluoride (PVDF) filter. Other sterilization methods like steam sterilization, gamma irradiation or ethylene oxide would degrade the polymer.
2. The rest of the excipients are dissolved in the same order of addition as in (0032), pH adjusted, and steam sterilized at 131 °C for 30 minutes.

3. The fraction in step 1 is added to the fraction in step 2 under continued magnetic stirring in a biosafety cabinet.
4. pH is verified and, if needed, adjusted to target pH±0.1 under a biosafety cabinet.
5. Final volume is completed with purified water under continued magnetic stirring under a biosafety cabinet with UV and laminar flow (BSL-2).
6. The formulations are filled in polypropylene vials at 2 mL each.

The stability study results at the different storage conditions (5±3 °C, 25 °C/60% RH, and 40 °C/75% RH) are shown in Tables 5-9 below:

TABLE 5

Solution appearance stability data [(a)]

| Storage Condition | Time (Weeks) | Formulation J | K | L | M |
|---|---|---|---|---|---|
| Tentative specification | | Clear and colorless solution | | | |
| Initial | 0 | X | X | X | X |
| 25 °C/60% RH | 6 | X | X | X | X |
| | 13 | X | X | X | X |
| 5 ± 3 C | 6 | X | X | X | X |
| | 13 | X | X | X | X |
| 40 °C/75% RH | 6 | X | X | X | X |
| | 13 | X | X | X | X |

[(a)] Analytical method: Visual observation.
X = met criteria, passed

TABLE 6 pH stability data [(a)]

| Storage Condition | Time (Weeks) | Formulation J | K | L | M |
|---|---|---|---|---|---|
| Tentative specifications | | 5.0-8.0 | | | |
| Initial | 0 | 7.0 | 6.9 | 6.0 | 7.1 |
| 25 °C/60% RH | 6 | 7.0 | 7.0 | 6.2 | 7.1 |
| | 13 | 7.0 | 7.0 | 6.3 | 7.2 |
| 5 ± 3 C | 6 | 7.0 | 7.0 | 6.2 | 7.1 |
| | 13 | 7.1 | 7.1 | 6.3 | 7.2 |
| 40 °C/75% RH | 6 | 7.0 | 7.0 | 6.2 | 7.1 |
| | 13 | 7.1 | 7.1 | 6.2 | 7.1 |

[(a)] Analytical method: USP <791>

TABLE 7

Osmolality stability data (mOsm/Kg) [(a, b)]

| Storage Condition | Time (Weeks) | Formulation J | K | L | M |
|---|---|---|---|---|---|
| Tentative specification | | 150-350 | | | |
| Initial | 0 | 192 | 252 | 264 | 213 |
| 25 °C/60% RH | 6 | — | — | — | — |
| | 13 | 207 | 249 | 243 | 243 |
| 5 ± 3 C | 6 | — | — | — | — |
| | 13 | 204 | 264 | 252 | 240 |
| 40 °C/75% RH | 6 | — | — | — | — |
| | 13 | 207 | 264 | 246 | 243 |

[(a)] Analytical Method: USP<785>;
[(b)] Due to the high formulation viscosity, the osmolality sample was diluted 3x in water for measurement

TABLE 8

Viscosity stability data [(a)]

| Storage Condition | Time (Weeks) | Formulation J [(b)] | K [(c)] | L [(d)] | M [(d)] |
|---|---|---|---|---|---|
| Tentative specification | | NMT 250 mPa · s | | | |
| Initial | 0 | 44.8 | 92.2 | 103.0 | 96.0 |
| 25 °C/60% RH | 6 | 42.2 | 89.6 | 99.2 | 92.2 |
| | 13 | 42.2 | 80.0 | 97.9 | 94.7 |
| 5 ± 3 C | 6 | 44.2 | 96.6 | 99.8 | 91.5 |
| | 13 | 46.1 | 95.4 | 101.8 | 92.8 |
| 40 °C/75% RH | 6 | 39.7 | 94.1 | 96.6 | 89.6 |
| | 13 | 41.0 | 94.7 | 97.3 | 92.8 |

[(a)] Analytical method: USP<912>. Testing conditions: chamber SC4-13RP; Spindle SC4-18; RPM 100; T: 21° C.);
[(b)] Torque: LT 10%;
[(c)] Torque LT 14%;
[(d)] Torque LT 15%

TABLE 9

TMC Structure Identification by FTIR [(a)]

| Storage Condition | Time (Weeks) | Formulation J | K | L | M |
|---|---|---|---|---|---|
| Tentative specification | | Report Data | | | |
| Initial | 0 | 64.4 | 64.7 | 63.9 | 60.2 |
| 25 °C/60% RH | 6 | 65.3 | 65.3 | 64.1 | 59.8 |
| | 13 | 63.1 | 63.1 | 63.9 | 61.6 |
| 40 °C/75% RH | 6 | — | — | — | — |
| | 13 | 63.3 | 64.3 | 64.7 | 63.5 |

[(a)] Analytical method: Fourier Transform Infrared (FTIR) spectroscopy. % Matching with the respective initial compound raw material (TMC)

The stability data in Tables 5-9 show that all tested formulations are physico-chemically stable (appearance, viscosity, pH, osmolality, and polymer chemical structure) over the study period (3 months) at all storage conditions tested (5±3 °C, 25 °C/60% RH, and 40 °C/75% RH).

Example 3

An in vitro study was conducted to determine the potential of chitosan and TMC in solution to inactivate the target virus in suspension, as per ASTM E1052-20, as a measure of virucidal effectiveness. Chitosan and TMC were evaluated individually at three concentrations (0.05%, 0.1%, and 0.15%) against viruses predominant in ophthalmic viral conjunctivitis and EKC. The four viruses evaluated in suspension were Adenovirus Type 3 (ADV-3), Adenovirus Type 4 (ADV-4), Adenovirus Type 7 (ADV-7), and Herpes Simplex Virus Type 1 (HSV-1). The test substances were spiked with the viruses, then titrated using a 50% tissue culture infectious dose ($TCID_{50}$) endpoint assay with A549 and Vero cells. All controls (neutralizer effectiveness/viral interference (NE/VI) and cytotoxicity (CT) for all viruses met the criteria for a valid test.

Figure 3A:
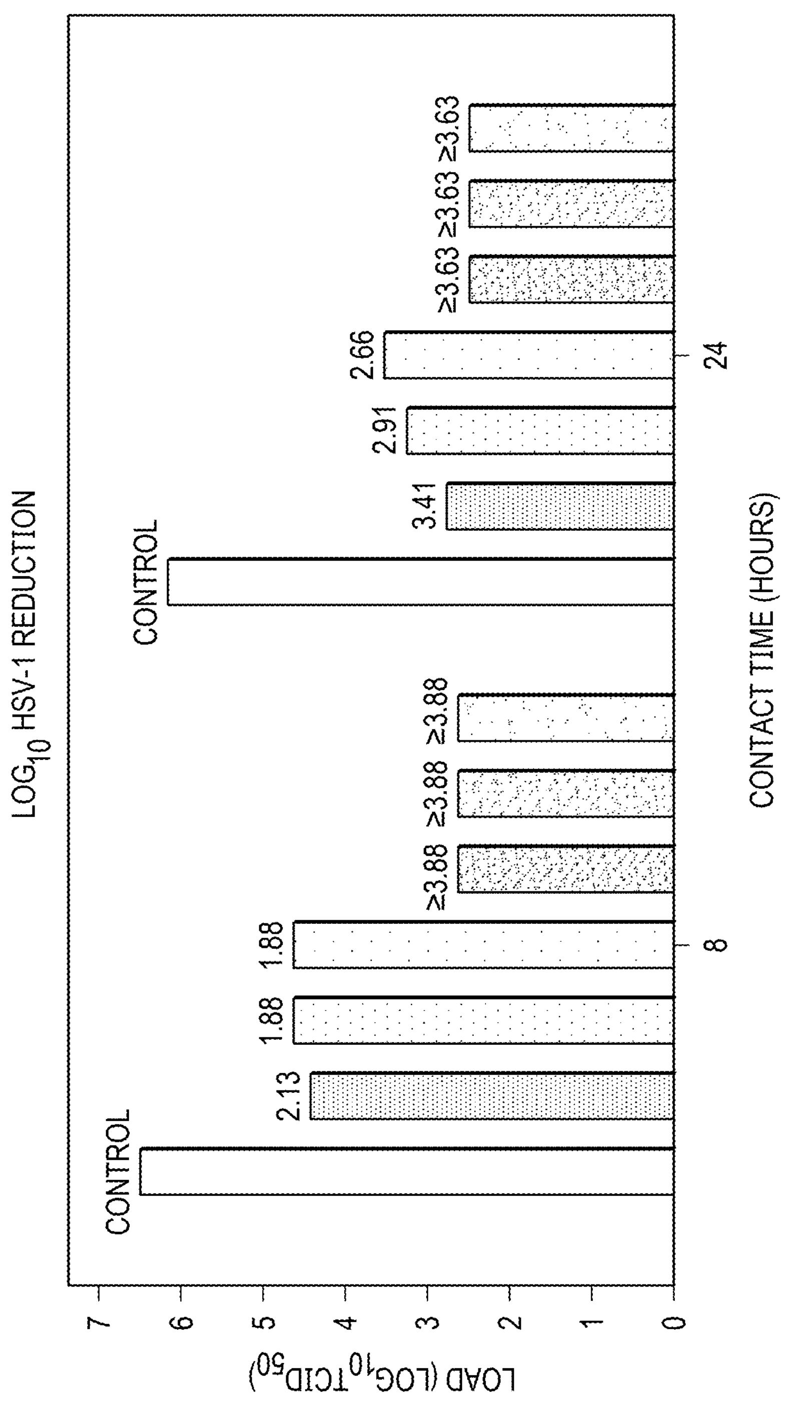
FIG. 3A illustrates a graphical presentation of Log 10 viral reduction of TMC and CS in all concentrations (0.05%, 0.1% and 0.15%) against HSV-1.
Figure 3B:
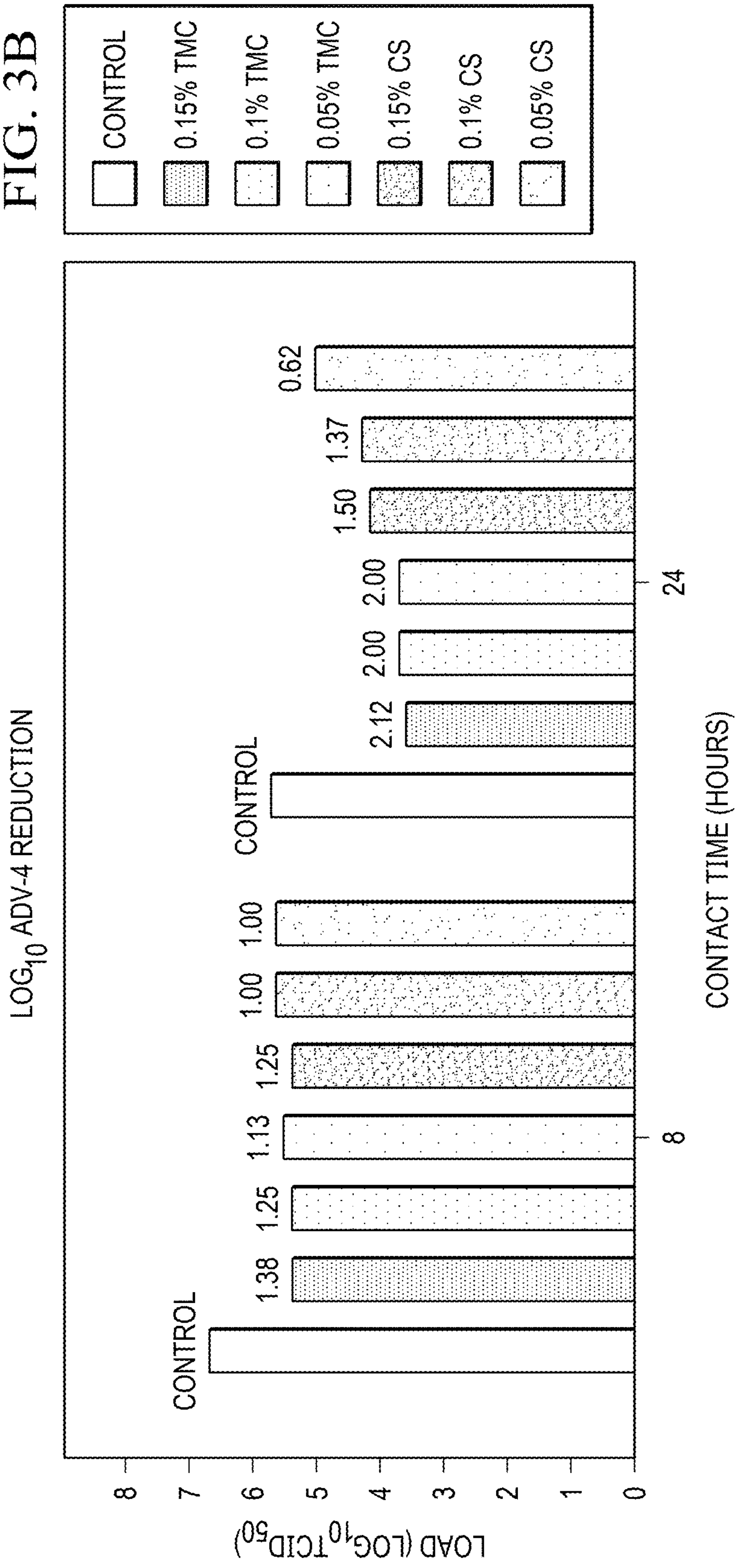
FIG. 3B illustrates a graphical representation of Log 10 viral reduction of TMC and CS in all concentrations (0.05%, 0.1% and 0.15%) against ADV-4 (N=3)

The results in FIGS. 3A and 3B show Log 10 reductions for chitosan and TMC against HSV-1 and ADV-4 at 8 and 24 hours of contact time. Log 10 reductions of TMC against HSV-1 (FIG. 3A) were most significant at 0.15% after 24 hours (3.45) and were comparable to chitosan at any concentration after 8 and 24 hours (≥3.63). Log 10 reductions against ADV-4 (FIG. 3B) show similar results between 0.15% TMC and chitosan at 8 hours; however, the reduction achieved by 0.15% TMC at 24 hours surpassed the results of chitosan at any concentration. Log 10 reductions for TMC against ADV-3 were ≥1 after 8 hours at 0.15%, compared with <1 at all contact times and concentrations for chitosan. Log 10 reductions for TMC and chitosan against ADV-7 were comparable, with reductions of ≤1.12 after 8 hours using 0.15% (data not shown).

Based on the in vitro antiviral efficacy study results, TMC demonstrates potent antiviral activity against HSV-1 and ADV-4 after a single dose or contact time.

Example 4

An in vitro study was conducted to determine the minimum inhibitory concentration (MIC) of chitosan derivatives, TMC and HTCC, for visible bacterial growth using the CLSI Broth Tube Dilution method. The two chitosan derivatives were evaluated at dilutions of 0.2%, 0.15%, 0.1%, 0.05%, 0.0125%, 0.0063%, 0.0031%, and 0.0016%, each inoculated with two bacterial strains commonly associated with ocular conjunctivitis. The bacterial strains evaluated were gram-negative *Pseudomonas aeruginosa* (ATCC 27853) and gram-positive *Staphylococcus aureus* (ATCC 29213).

Antibacterial activity results, presented in TABLE 9, show that TMC is highly effective and superior to HTCC at reducing bacterial loads of gram-negative and gram-positive bacteria.

TABLE 10

| Compound | Microorganism | Negative Control [(a)] | Positive Control [(b)] | MIC | Inocula Final Concentration (CFU/mL) |
|---|---|---|---|---|---|
| TMC | *Pseudomonas aeruginosa* | No Growth | Growth | 0.0125% | $2.3 \times 10^6$ |
| HTCC | (ATCC 27853) | No Growth | Growth | 0.05% | $2.3 \times 10^6$ |
| TMC | *Staphylococcus aureus* | No Growth | Growth | 0.0031% | $2.2 \times 10^6$ |
| HTCC | (ATCC 29213) | No Growth | Growth | 0.0063% | $2.2 \times 10^6$ |

[(a)] Mueller-Hinton Broth (MHB) each compound;
[(b)] Microorganism under study

In certain embodiments, the minimum inhibitory concentration (MIC) of TMC is estimated to be approximately ten times higher than that of standard-of-care (SOC) antibiotic treatments, such as Moxifloxacin, which exhibits an $MIC_{90}$ of 0.000252% against *Staphylococcus aureus*. Despite a higher MIC, TMC offers superior clinical and safety advantages over SOC antibiotics due to its distinct mechanism of action. TMC functions by ionically binding to microbial cell walls and physically disrupting the microorganisms' structural integrity, rather than interfering with biochemical or genetic pathways targeted by conventional antibiotics. This non-specific, physical mode of antimicrobial activity minimizes or eliminates the development of antibiotic resistance commonly associated with overuse or non-compliance of SOC treatments. Accordingly, the use of TMC provides an improved therapeutic approach that combines effective antimicrobial activity with a substantially reduced risk of resistance development, thereby offering enhanced safety and long-term clinical utility compared to existing SOC antibiotics.

TMC demonstrates potent in vitro antibacterial activity against Gram-positive and Gram-negative bacteria, as shown in TABLE 10.

Example 5

The same methodology as in EXAMPLE 4 was used to determine the MIC of TMC and HTCC against two fungal strains common in ocular fungal conjunctivitis and keratitis: *Aspergillus brasiliensis* (ATCC 16404) and *Fusarium keratoplasticum* (ATCC 36031) found in fungal conjunctivitis.

Results of antifungal activity, presented in TABLE 10, show that TMC is also highly effective and superior to HTCC in reducing fungal load.

TABLE 11

| Compound | Microorganism | Negative Control [(a)] | Positive Control [(b)] | MIC | Inocula Final Concentration (CFU/mL) |
|---|---|---|---|---|---|
| TMC | *Aspergillus brasiliensis* | No Growth | Growth | 0.0031 | $1.3 \times 10^4$ |
| HTCC | (ATCC 16404) | No Growth | Growth | >0.2% | $1.3 \times 10^4$ |
| TMC | *Fusarium keratoplasticum* | No Growth | Growth | <0.0016 | $2.1 \times 10^4$ |
| HTCC | (ATCC 36031) | No Growth | Growth | 0.15% | $2.1 \times 10^4$ |

[(a)] Mueller-Hinton Broth (MHB), each compound;
[(b)] Microorganism under study The MIC of TMC is comparable to Natamycin, the only topical antifungal ocular drug approved by the US FDA. The $MIC_{90}$ of Natamycin is 0.0008% for *Fusarium keratoplasticum* and 0.0032% for *Aspergillus brasiliensis.*

Natamycin is commercially available as a 5% w/v topical ocular suspension with low bioavailability (<5%) and a high dosing frequency, and it may cause minor irritation and discomfort. The posology is 1 drop every 1-2 h for the first 3-4 days, followed by 6-8 times daily for 14-21 days. The long dosing schedule of Natamycin suspension with shorter residence time at the site of action causes failure of therapy and an increase in resistance to fungal keratitis.

TMC demonstrates potent in vitro antifungal activity, as shown in TABLE 10, and a better safety profile than Natamycin.

Example 6

An in vitro study was designed to evaluate the anti-biofilm activity of formulation-J against biofilms on contact lenses. Biofilm is a microbial community that can adhere to biotic or abiotic surfaces and produce extracellular polysaccharides. The microbial cells that grow in a biofilm are physiologically distinct from planktonic cells of the same organism and are more resistant to antibiotics, disinfectants, or the host's defense mechanisms. Development of mature biofilms on contact lenses has been associated with keratitis in humans and animal models. Disinfection plays a vital role in preventing contact lens-related infections, as contact lenses can increase the risk of microbial adhesion and biofilm formation.

Biofilms of methicillin-resistant *Staphylococcus aureus* (MRSA) and *Pseudomonas aeruginosa* were generated on the surface of a commercially available brand of contact lenses. Three contaminated lenses per microorganism were evaluated using one lot of TMC formulation-J at 0.15% concentration and at four contact times (<30 seconds, 6, 24, and 48 hours) at 36±1 °C. After each contact time, the lenses were washed with a neutralizer solution and vortex-mixed with glass beads to remove biofilm and disaggregate clumps. The cell suspension was serially diluted and recovered in agar medium. Three contaminated lenses per microorganism per contact time were exposed to a buffer solution and processed similarly to the treated lenses, serving as an untreated control. The treated and untreated control Log 10 densities (CFU/carrier) were used to calculate the log reductions.

Figure 4:
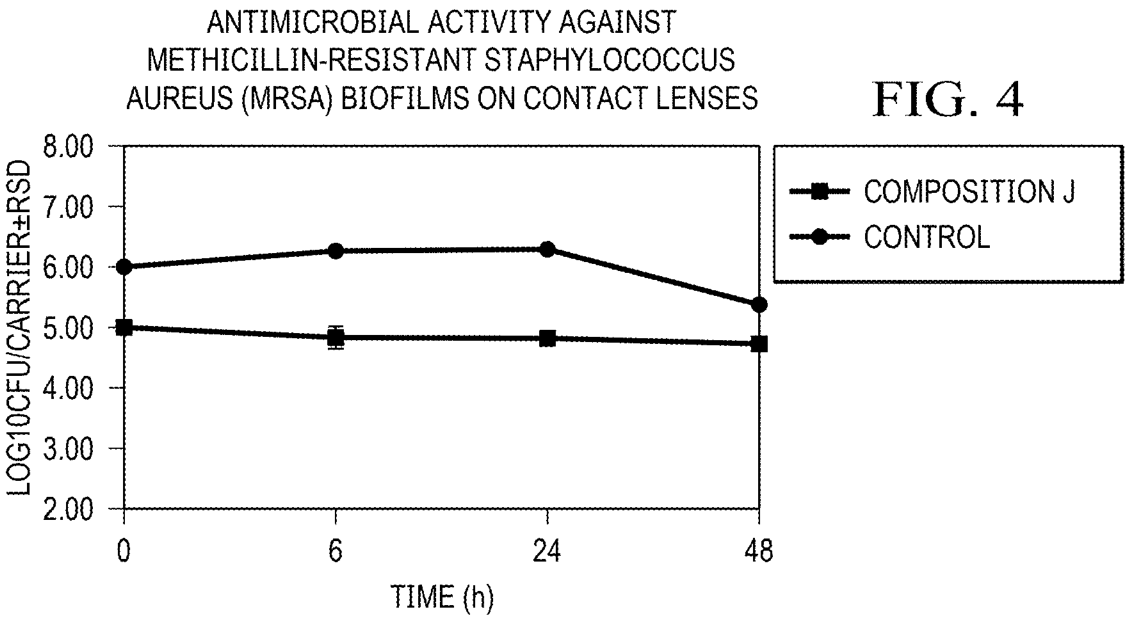
FIG. 4 illustrates a graphical presentation of the TMC 0.15% solution (Composition J) activity against Methicillin-Resistant *Staphylococcus Aureus* (MRSA) biofilms on contact lenses.
Figure 5:
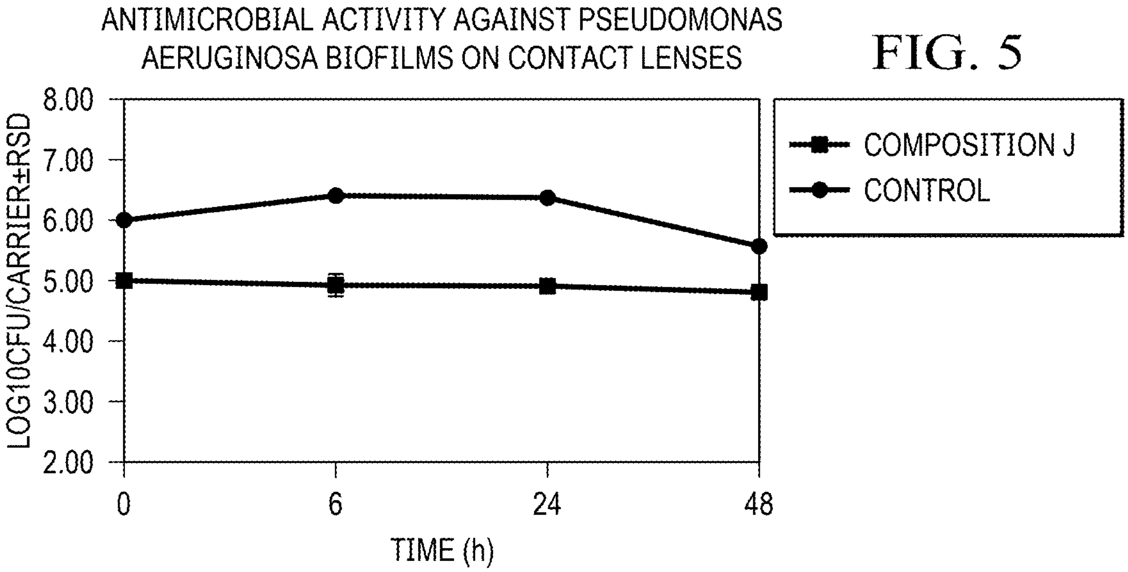
FIG. 5 illustrates a graphical presentation of the TMC 0.15% solution (Composition J) activity against *Pseudomonas aeruginosa* biofilms on contact lenses.

In vitro antimicrobial activity of Formulation J (TMC 0.15% final solution) against MRSA and *P. aeruginosa* biofilm on contact lenses over time is presented in FIGS. 4 and 5, respectively. All controls met the test criteria established for a valid test.

Formulation J (TMC, 0.15%) showed activity against *P. aeruginosa* biofilm, with a 1.5 $log_{10}$ reduction at 30 seconds and a 1.79 $log_{10}$ reduction at 48 hours, as well as against MRSA biofilm with a 1.5 $log_{10}$ reduction at 6 hours. For ophthalmic eyedrop products intended for direct ocular dosing (2-3 times daily while wearing contact lenses), a 1.5 $log_{10}$ reduction after a single application indicates the potential to reduce or prevent biofilm for 24-48 hours.

Appendix

FORMULA-I

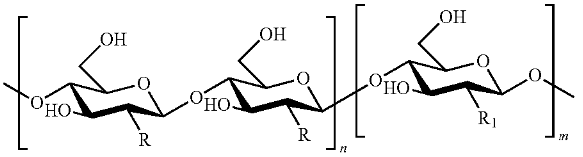

Where:

R=

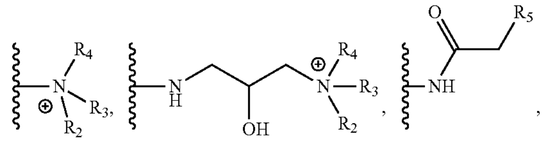

$R_1$=$NH_2$ or $NHC(O)CH_3$ $R_2$=$R_3$=$R_4$=Alkyl defined as $CH_3$, $C_2H_5$, $C_3H_7$; substituted alkyl defined as —$C_2H_5$—$(CH_2)_x$—OH, $C_2H_5$—$(CH_2)$x-$NHR_6$; cycloalkyl.

$R_5$=Pyridinium, substituted pyridinium, $R_6$=alkyl, aryl. x=1-5

Representative Classes of Molecules:

When:

R=

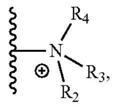

$R_1$=$NH_2$ $R_2$=$R_3$=$R_4$=Alkyl defined as $CH_3$, $C_2H_5$, $C_3H_7$; substituted alkyl defined as —$C_2H_5$—$(CH_2)$x-OH, $C_2H_5$—$(CH_2)$x-$NHR_6$; cycloalkyl.

$R_6$=alkyl, aryl. x=1-5

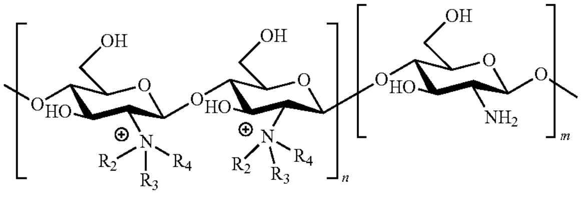

Specifically, when $R_2=R_3=R_4=CH_3$, and $R_1=NH_2$

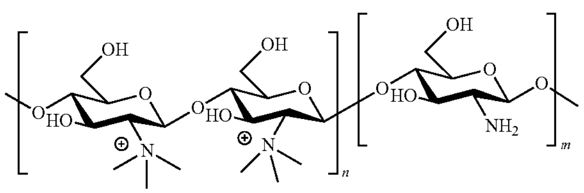

Trimethyl Chitosan (TMC)

When:

R=

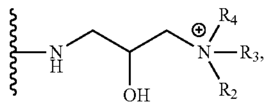

$R_1=NH_2$ $R_2=R_3=R_4$=Alkyl defined as $CH_3$, $C_2H_5$, $C_3H_7$; substituted alkyl defined as $-C_2H_5-(CH_2)x-OH$, $C_2H_5-(CH_2)x-NHR_6$; cycloalkyl.

$R_6$=alkyl, aryl. x=1-5

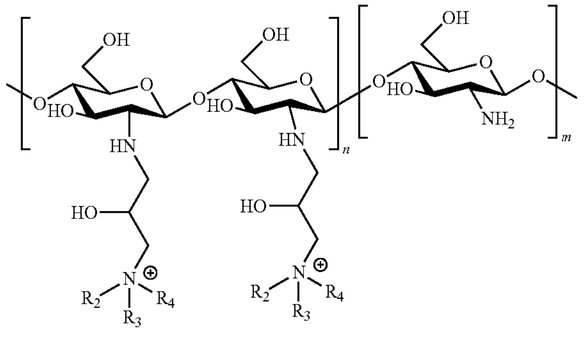

Specifically, when $R_2=R_3=R_4=CH_3$, and $R_1=NH_2$

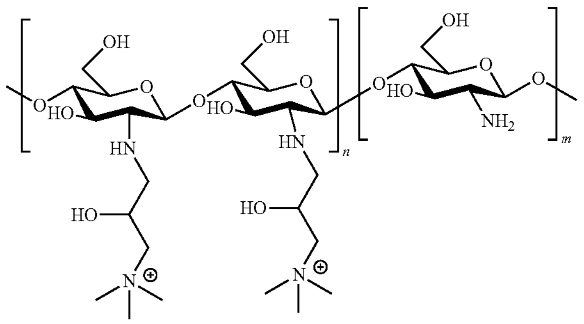

N-(2-Hydroxy) propyl-3-trimethylammonium chitosan (HTCC)

When:

R=

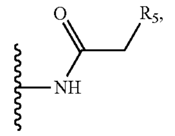

$R_1=NHC(O)CH_3$ $R_5$=Pyridinium, substituted pyridinium

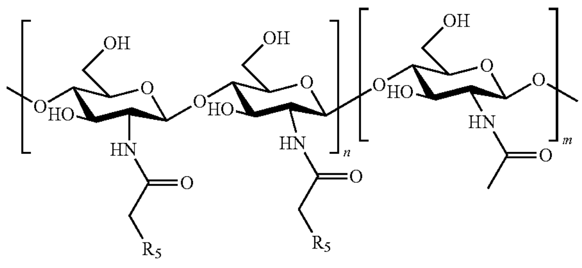

Specifically, when, $R_1=NHC(O)CH_3$, $R_5$=Pyridinium

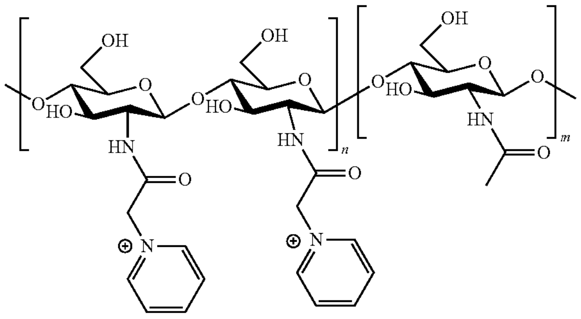

(2-pyridinium)acetyl chitosan (PACS)

It will be appreciated by those skilled in the art, having the benefit of this disclosure, that this is a Sterile Aqueous Ophthalmic Solution Containing Quaternary Chitosan Derivatives. It should be understood that the drawings and detailed description herein are to be regarded in an illustrative rather than a restrictive manner, and are not intended to be limiting to the particular forms and examples disclosed. On the contrary, included are any further modifications, changes, rearrangements, substitutions, alternatives, design choices, and embodiments apparent to those of ordinary skill in the art, without departing from the spirit and scope hereof, as defined by the following claims. Thus, it is intended that the following claims be interpreted to embrace all such further modifications, changes, rearrangements, substitutions, alternatives, design choices, and embodiments.

What is claimed is:

1. A pharmaceutical composition to be applied to an ocular surface for direct ocular dosing comprising:

a positively charged quaternary chitosan derivative as an active ingredient to provide antimicrobial activity against at least one of gram-negative bacteria, gram-positive bacteria, fungi, and viruses, wherein the quaternary chitosan derivative comprising at least one of trimethyl chitosan (TMC) or N-(2-hydroxy) propyl-3-trimethylammonium chitosan chloride (HTCC);

a non-ionic cellulose compound acting as a viscosity agent and demulcent to protect and lubricate mucous membrane surfaces;

a non-ionic humectant and tonicity agent to retain moisture on the ocular surface, and maintain a comfortable osmolarity for the eye within a range of 150-350 mOsm/Kg;

a low ionic strength buffer/pH adjuster system configured to maintain a physiologically tolerable pH of about 6.0 to 8.0;

wherein the degree of quaternization loss of the TMC is not more than ten percent for at least 13 weeks at 25 °C/60% RH (Relative Humidity) and 40 °C/75% RH (Relative Humidity);

wherein the pharmaceutical composition comprising the quaternary chitosan derivative has an extended in vitro antiviral activity compared to antiviral activity of a pharmaceutical composition comprising chitosan; and purified water as a diluent.

2. The pharmaceutical composition of claim 1, wherein the quaternary chitosan derivative is present at a concentration of 0.05% to 0.2% w/w.

3. The pharmaceutical composition of claim 1, wherein the cellulose compound is comprised of hydroxypropyl methylcellulose (HPMC).

4. The pharmaceutical composition of claim 1, wherein the cellulose compound is nonionic comprised of hydroxyethyl cellulose (HEC).

5. The pharmaceutical composition of claim 1, wherein the humectant and tonicity agent comprises polyethylene glycol 400.

6. The pharmaceutical composition of claim 5, wherein Polyethylene glycol 400 is incorporated at a 2.6% concentration, which is the maximum concentration to be used within the osmolality range 220-320 mOsm/Kg.

7. The pharmaceutical composition of claim 6, and further comprising mannitol as a tonicity agent to adjust the osmolarity.

8. The pharmaceutical composition of claim 1, wherein the tonicity agents comprise Polyols as tonicity agents selected from the group of Mannitol, Glycerol and Sorbitol and the maximum concentrations to be used within the osmolality range 220-320mOsm/Kg are the following: Mannitol 5.4%, Glycerol 2.9% and Sorbitol 5.4%.

9. The pharmaceutical composition of claim 1, wherein the low ionic strength buffer/pH adjuster system incorporates boric acid as the buffer.

10. The pharmaceutical composition of claim 9, wherein low ionic strength buffer/pH adjuster system incorporates Hydrochloric Acid as a pH adjuster.

11. The pharmaceutical composition of claim 9, wherein low ionic strength buffer/pH adjuster system incorporates Sodium Hydroxide as a pH adjuster.

12. A pharmaceutical composition to be applied to an ocular surface for direct ocular dosing comprising:

a quaternary chitosan derivative as an active ingredient to provide antimicrobial activity against at least one of gram-negative bacteria, gram-positive bacteria, fungi, and viruses in a concentration of 0.01% to 1% w/w, wherein the quaternary chitosan derivative comprising at least one of trimethyl chitosan (TMC) or N-(2-hydroxy) propyl-3-trimethylammonium chitosan chloride (HTCC);

a non-ionic cellulose compound acting as a viscosity agent and demulcent to protect and lubricate mucous membrane surfaces in a concentration of 0.5-1.0% w/w;

a non-ionic humectant and tonicity agent to retain moisture on the ocular surface, and maintain a comfortable osmolarity for the eye within 220-320 mOsm/Kg, the non-ionic humectant and tonicity agent comprising:

polyethylene glycol 400 in a concentration of 0.5-1.5% w/w, and mannitol in a concentration of 1-3% w/w;

a low ionic strength buffer/pH adjuster system configured to maintain a physiologically tolerable pH of about 6.0 to 8.0 comprised of boric acid with a concentration of 0.1-1.5% w/w;

wherein the degree of quaternization loss of the TMC is not more than percent for at least 13 weeks at 25 °C/60% RH (Relative Humidity) and 40 °C/75% RH (Relative Humidity);

wherein the pharmaceutical composition comprising the quaternary chitosan derivative has an extended in vitro antiviral activity compared to antiviral activity of a pharmaceutical composition comprising chitosan; and purified water as a diluent q.s. to 100%.

13. The pharmaceutical composition of claim 12, wherein the cellulose compound is comprised of hydroxypropyl methylcellulose (HPMC).

14. The pharmaceutical composition of claim 12, wherein the cellulose compound is nonionic comprised of hydroxyethyl cellulose (HEC).

15. The pharmaceutical composition of claim 12, wherein the humectant and tonicity agent comprises polyethylene glycol 400.

16. The pharmaceutical composition of claim 12, wherein the low ionic strength buffer/pH adjuster system incorporates boric acid as the buffer.

17. The pharmaceutical composition of claim 16, wherein low ionic strength buffer/pH adjuster system incorporates Hydrochloric Acid as a pH adjuster.

18. The pharmaceutical composition of claim 16, wherein low ionic strength buffer/pH adjuster system incorporates Sodium Hydroxide as a pH adjuster.

19. A method of treating conjunctivitis in a subject in need thereof, comprising the steps of administering to the subject an effective amount of the pharmaceutical composition of claim 1.

20. The method of claim 19, wherein the conjunctivitis is adenoviral conjunctivitis or epidemic keratoconjunctivitis (EKC).

21. The method of claim 19, wherein the conjunctivitis is bacterial conjunctivitis caused by *Staphylococcus aureus* or *Pseudomonas aeruginosa.*

22. The method of claim 19, wherein the conjunctivitis is fungal conjunctivitis or keratitis caused by *Aspergillus brasiliensis* or *Fusarium* keratoplasticum.

23. The method of claim 19, wherein the administration prevents or reduces biofilm formation on the ocular surface or on contact lenses.

24. The solution of claim 1, wherein the formulation exhibits at least a 1.5 log 10 reduction in biofilm density of *Pseudomonas aeruginosa* or *Staphylococcus aureus* within 24 hours.

25. The solution of claim 1, wherein the quaternary chitosan derivative maintains antiviral activity against adenovirus type 3, 4, 7, or HSV-1 in vitro.

26. A pharmaceutical composition in the form of an eye drop for delivering an active ingredient to an ocular surface via direct ocular dosing, comprising:

an eye drop solution comprising:

a non-ionic cellulose compound acting as a viscosity agent and demulcent to protect and lubricate mucous membrane surfaces in a concentration of 0.5-1.0% w/w, a non-ionic humectant and tonicity agent to retain moisture on the ocular surface, and maintain a comfortable osmolarity for the eye within 220-320 mOsm/Kg, the non-ionic humectant and tonicity agent comprising:

polyethylene glycol 400 in a concentration of 0.5-1.5% w/w, and mannitol in a concentration of 1-3% w/w, a low ionic strength buffer/pH adjuster system configured to maintain a physiologically tolerable pH of about 6.0 to 8.0 comprised of boric acid with a concentration of 0.1-1.5% w/w, and purified water as a diluent q.s. to 100%; and the active ingredient comprising a quaternary chitosan derivative in solution with the eyedrop to provide antimicrobial activity against at least one of gram-negative bacteria, gram-positive bacteria, fungi, and viruses in a concentration of 0.01% to 1% w/w, wherein the quaternary chitosan derivative comprising at least one of trimethyl chitosan (TMC) or N-(2-hydroxy) propyl-3-trimethylammonium chitosan chloride (HTCC);

wherein the degree of quaternization loss of the TMC is not more than ten percent for at least 13 weeks at 25 °C/60% RH (Relative Humidity) and 40 °C/75% RH (Relative Humidity);

wherein the pharmaceutical composition comprising the quaternary chitosan derivative has an extended in vitro antiviral activity compared to antiviral activity of a pharmaceutical composition comprising chitosan; and wherein the eye drop solution minimizes degradation of the active ingredient in solution.

* * * * *